(12) United States Patent
Walter et al.

(10) Patent No.: US 7,851,410 B2
(45) Date of Patent: Dec. 14, 2010

(54) HERBICIDAL COMPOSITION

(75) Inventors: James Walter, West Chester, PA (US);
Frank Robert Walls, Jr., Goldsboro, NC (US); James T. Bahr, Hopewell, NJ (US)

(73) Assignee: FMC Corporation, Philadelphia, PA (US)

( * ) Notice: Subject to any disclaimer, the term of this patent is extended or adjusted under 35 U.S.C. 154(b) by 204 days.

(21) Appl. No.: 12/373,859

(22) PCT Filed: Jul. 13, 2007

(86) PCT No.: PCT/US2007/073427

§ 371 (c)(1),
(2), (4) Date: Jan. 14, 2009

(87) PCT Pub. No.: WO2008/008932

PCT Pub. Date: Jan. 17, 2008

(65) Prior Publication Data

US 2010/0009849 A1    Jan. 14, 2010

(60) Provisional application No. 60/830,858, filed on Jul. 14, 2006.

(51) Int. Cl.
*A01N 43/00* (2006.01)
(52) U.S. Cl. .................................................... 504/139
(58) Field of Classification Search .................. 504/139
See application file for complete search history.

(56) References Cited

U.S. PATENT DOCUMENTS 3,764,623 A    10/1973    Hunter et al.
4,818,275 A    4/1989    Theodoridis

*Primary Examiner*—Alton N Pryor

(57) ABSTRACT

The present invention provides an herbicidal composition comprising a first herbicide and a second herbicide in which the first herbicide is 2,4-dinitro-$N^3,N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide and a method of use.

6 Claims, No Drawings

HERBICIDAL COMPOSITION

This application claims the benefit of U.S. Provisional Application No. 60/830,858, filed Jul. 14, 2006.

FIELD OF THE INVENTION

This invention relates to herbicidal compositions containing an 2,4-dinitro-$N^3,N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide.

BACKGROUND OF THE INVENTION

U.S. Pat. No. 3,764,623 discloses Herbicidal Dinitro-1,3-Phenylenediamine Compounds. U.S. Pat. No. 4,818,275 discloses Herbicidal Aryl Triazolinones.

SUMMARY OF THE INVENTION

In accordance with the present invention, it has been found that an herbicidal composition comprising a first herbicide and a second herbicide in which the first herbicide is 2,4-dinitro-$N^3,N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide, wherein the first herbicide and the second herbicide are present in an herbicidal effective amount, has unexpected advantageous properties over the individual components.

DETAILED DESCRIPTION OF THE INVENTION

It has been unexpectedly found that an herbicidal composition comprising a first herbicide and a second herbicide in which the first herbicide is 2,4-dinitro-$N^3,N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide has advantageous properties in weed control over the individual components, for example the mixture controls a broader variety of weeds at lower rates than either component alone.

The structural formula of 2,4-dinitro-$N^3,N^3$-dipropyl-6-(trifluoromethyl)-1,3-benzenediamine is as follows:

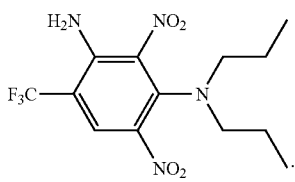

The structural formula for N-[2,4-dichloro-5-[4-(difluoromethyl)-4,5-dihydro-3-methyl-5-oxo-1H-1,2,4-triazol-1-yl]phenyl]methanesulfonamide is as follows:

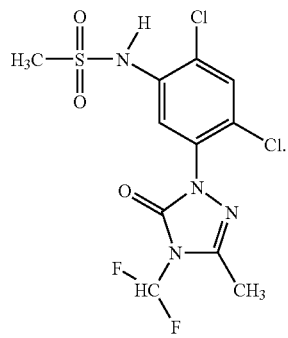

The ratio of 2,4-dinitro-$N^3,N^3$-dipropyl-6-(trifluoromethyl)-1,3-benzenediamine to N-[2,4-dichloro-5-[4-(difluoromethyl)-4,5-dihydro-3-methyl-5-oxo-1H-1,2,4-triazol-1-yl]phenyl]methanesulfonamide varies over a wide range but is usually in the range 10:1 to 1:1, preferably 7:1 to 2:1.

Other herbicides can be employed in conjunction with the first and second herbicides described above providing they do not adversely affect the interaction between the components of this invention. For example it can sometimes be useful to include additional herbicides to extend the range of activity in order to control a wider spectrum of weeds.

Another embodiment of the present invention is a method for controlling broadleaf and grass weeds in crops or turf which comprises applying a composition of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide, either together or sequentially, to a locus where weeds are present or are expected to be present.

The compositions of the present invention may be employed in many forms and are often most conveniently prepared in aqueous form immediately prior to use. One method of preparing such a composition is referred to as "tank mixing" in which the ingredients in their commercially available form, either with or without other additives, are mixed together by the user in a quantity of water.

In addition to tank mixing immediately prior to use the compositions containing 2,4-dinitro-$N^3,N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide may be formulated into a more concentrated primary composition which is diluted with water or other diluent before use. Such compositions may comprise a surface active agent in addition to the active ingredients and examples of such compositions are set forth below.

The herbicidal compounds of the present invention may be formulated as a granule of relatively large particle size (for example, 8/16 or 4/8 US Mesh), on fertilizer granules, as water-soluble or water-dispersible granules, as powdery dusts, as wettable powders, as emulsifiable concentrates, as aqueous emulsions, as solutions, or as any of the other known types of agriculturally-useful formulations, depending on the desired mode of application to the areas in which suppression of vegetation is desired. These formulations may contain as little as 0.1%, 0.2% or 0.5% to as much as 95% or more by weight of the total of the two herbicides.

The composition can be in the form of a dispersible solution which comprises the herbicides dissolved in a water-miscible solvent with the addition of a dispersing agent. Alternatively it can comprise the herbicides in the form of a finely ground powder in association with a dispersing agent and intimately mixed with water to give a paste or cream which can if desired be added to an emulsion of oil in water to give a dispersion of the two herbicides in an aqueous oil emulsion.

Alternatively, the composition can be in the form of water-soluble or water-dispersible granules that disperse readily in water or other dispersant. Water-soluble or water-dispersible granules normally are prepared to contain about 5-80% of the herbicides, depending on the absorbency of the carrier, and usually also contain a wetting, dispersing or emulsifying agent to facilitate dispersion and may contain a preservative. Typical carriers for water-soluble or water-dispersible granules include Fuller's earth, natural clays, silicas, and other highly absorbent, readily wet inorganic diluents. For example, a useful water-soluble or water-dispersible granule formulation contains 26.71 parts of the herbicidal compound, 30.90 parts of ammonium sulfate, 30.89 parts of continental clay, 10.00 parts of sodium lignosulfonate as a dispersant, 1.00 part of sodium dioctylsuccinate as a wetting agent and 0.50 part of citric acid as a preservative. The mixture is milled, diluted with water to form a paste and the paste is extruded and dried to produce granules.

Other alternatives that may be employed are dusts which are free flowing admixtures of the herbicides with finely divided solids such as talc, natural clays, kieselguhr, flours such as walnut shell and cottonseed flours, and other organic and inorganic solids which act as dispersants and carriers for the herbicides. These finely divided solids have an average particle size of less than about 50 microns. A typical dust formulation useful herein is one containing 1.0 part or less of the herbicidal compounds and 99.0 parts of talc.

Also useful formulations for the herbicidal compositions of the present invention are wettable powders in the form of finely divided particles that disperse readily in water or other dispersant. The wettable powder is ultimately applied to the locus where weed control is needed either as a dry dust or as an emulsion in water or other liquid. Typical carriers for wettable powders include Fuller's earth, kaolin clays, silicas, and other highly absorbent, readily wet inorganic diluents. Wettable powders are prepared to contain about 5-80% of the herbicides, depending on the absorbency of the carrier, and usually also contain a small amount of a wetting, dispersing or emulsifying agent to facilitate dispersion. For example, a useful wettable powder formulation contains 80.0 parts of the herbicidal compounds, 17.9 parts of Palmetto clay, and 1.0 part of sodium lignosulfonate and 0.3 part of sulfonated aliphatic polyester as wetting agents. Additional wetting agents and/or oils will frequently be added to a tank mix to facilitate dispersion on the foliage of the plant.

Other useful formulations for the herbicidal compositions of the present invention are emulsifiable concentrates (ECs) which are homogeneous liquid compositions dispersible in water or other dispersant, and may consist entirely of the herbicidal compounds and a liquid or solid emulsifying agent, or may also contain a liquid carrier, such as xylene, heavy aromatic naphthas, isophorone, or other non-volatile organic solvents. For herbicidal application these concentrates are dispersed in water or other liquid carriers and applied as a spray to the area to be treated. The percentage by weight of the herbicidal compounds may vary according to the manner in which the composition is to be applied, but in general comprises 0.5 to 95% of the herbicidal compounds by weight of the total composition.

Suspension concentrate formulations may also be employed. These are similar to ECs, except that the herbicidal compounds are suspended in a liquid carrier, generally water. Suspension concentrates, like ECs, may include a small amount of a surfactant, and will typically contain the herbicidal compounds in the range of 0.5 to 95%, frequently from 10 to 50%, by weight of the total composition. For example, a useful suspension concentrate formulation contains 22.0 parts of the herbicidal compounds, 2.6 parts of an ethoxylated/propoxylated block copolymer surfactant, 0.4 part phosphate ester surfactant, 0.8 part thickening agent, 6.0 parts antifreeze agent, 0.1 antifoam agent, 0.05 part anti-bactericide and 44.0 parts distilled water. For herbicidal application, suspension concentrates may be diluted in water or other liquid vehicle, and are normally applied as a spray to the area to be treated.

Other useful formulations include suspensions of the herbicidal compounds in a relatively non-volatile solvent such as water, corn oil, kerosene, propylene glycol, or other suitable solvents.

Still other useful formulations for these herbicidal compositions include simple solutions of the herbicides in a solvent in which it is completely soluble at the desired concentration, such as acetone, alkylated naphthalenes, xylene, or other organic solvents. Granular formulations, wherein the herbicides are carried on relative coarse particles, are of particular utility for aerial distribution or for penetration of cover crop canopy. Pressurized sprays, typically aerosols wherein the herbicides are dispersed in finely divided form as a result of vaporization of a low-boiling dispersant solvent carrier may also be used.

In some circumstances it may be desirable to combine two types of formulation e.g. one of the herbicidal compounds is used as an emulsifiable concentrate and the second herbicidal compound is dispersed as a powder in this concentrate.

The concentrate of the first and second herbicides (when used as the sole active components) in a composition for direct application to the crop by conventional ground methods is preferably within the range of 0.001 to 10% by weight of the composition, especially 0.005 to 5% by weight, but more concentrated compositions containing up to 40% may be desirable.

Typical wetting, dispersing or emulsifying agents that may be used in the compositions of the present invention include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

The invention is illustrated in the following Examples which describe experiments in which a beneficial effect was observed.

Example 1

Pre-emergent herbicidal evaluation of 2,4-dinitro-$N^3$, $N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl] methanesulfonamide on Spurge The compositions of the present invention were tested for herbicidal efficacy in the following manner:

Test compositions were prepared of i) a granular fertilizer and 2,4-dinitro-$N^3$,$N^3$-dipropyl-6-(trifluoromethyl)-1,3-benzenediamine, and ii) a granular fertilizer and N-[2,4-dichloro-5-[4-(difluoromethyl)-4,5-dihydro-3-methyl-5-oxo-1H-1,2,4-triazol-1-yl]phenyl]methanesulfonamide. The test compositions were prepared to provide the desired application rates of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide. In addition, test compositions were prepared containing mixtures of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide with granular fertilizer that provided the specified rates of the two herbicides.

The experimental design used randomized plots with one pre-emergent treatment either the day of planting or the day after planting and three to four replications per test trial. The size of each experimental plot was 6 feet by 30 feet.

Percent control of the weed (Spurge) was evaluated and averaged in each experimental plot at 70 days after treatment (DAT) of each test rate.

The results, shown as an average of the replications, were compared with results observed in untreated control plots in the same trials. The results are in Table 1 below.

TABLE 1

Control of Spurge by Compositions of the Present Invention

| Treatment | Rate of Appln. (lb AI/Acre) | Control @ 70 DAT (%) |
|---|---|---|
| A | 0.125 | 0 |
|  | 0.250 | 6 |
|  | 0.375 | 6 |
| B | 0.50 | 42 |
|  | 0.75 | 70 |
|  | 1.00 | 60 |
| A + B | 0.125/0.50 | 72 |
|  | 0.125/0.75 | 82 |
|  | 0.125/1.00 | 80 |
|  | 0.250/0.50 | 70 |
|  | 0.250/0.75 | 74 |
|  | 0.250/1.00 | 80 |
|  | 0.375/0.50 | 74 |
|  | 0.375/0.75 | 78 |
|  | 0.375/1.00 | 90 |
| Untreated |  | 0 |

A = N-[2,4-dichloro-5-[4-(difluoromethyl)-4,5-dihydro-3-methyl-5-oxo-1H-1,2,4-triazol-1-yl]phenyl]methanesulfonamide
B = 2,4-dinitro-$N^3$,$N^3$-dipropyl-6-(trifluoromethyl)-1,3-benzenediamine Example 2

Pre-emergent herbicidal evaluation of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide on Goose Grass The compositions of the present invention were tested for herbicidal efficacy in the following manner:

Test compositions were prepared by dilution of a 65% water-soluble granule (65 WG) formulation of 2,4-dinitro-$N^3$,$N^3$-dipropyl-6-(trifluoromethyl)-1,3-benzenediamine in a spray tank that provided the appropriate application rate of 2,4-dinitro-$N^3$,$N^3$-dipropyl-6-(trifluoromethyl)-1,3-benzenediamine. Test compositions were also prepared by dilution of a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide in a spray tank that provided the appropriate application rate of N-[2,4-dichloro-5-[4-(difluoromethyl)-4,5-dihydro-3-methyl-5-oxo-1H-1,2,4-triazol-1-yl]phenyl]methanesulfonamide. In addition, test compositions were prepared containing mixtures of a 65% water-soluble granule (65 WG) formulation of 2,4-dinitro-$N^3$,$N^3$-dipropyl-6-(trifluoromethyl)-1,3-benzenediamine and a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide with water that provided the specified rates of the two herbicides.

The application of each test composition was performed with pressurized back-pack sprayers, calibrated to spray between 10 and 15 gallons per acre.

The experimental design used randomized plots with one pre-emergent treatment either the day of planting or the day after planting and four to eight replications per test trial. The size of each experimental plot was 6 feet by 30 feet.

Percent control of the weed (Goose Grass) was evaluated and averaged in each experimental plot at 14 days after treatment (DAT) of each test rate.

The results, shown as an average of the replications, were compared with results observed in untreated control plots in the same trials. The results are in Table 2 below.

TABLE 2

Control of Goose Grass by Compositions of the Present Invention

| Treatment | Rate of Appln. (lb AI/Acre) | Control @ 14 DAT (%) |
|---|---|---|
| A | 0.06 | 49 |
|  | 0.12 | 69 |
|  | 0.19 | 77 |
|  | 0.25 | 79 |
| B | 0.12 | 76 |
|  | 0.25 | 99 |
|  | 0.50 | 100 |
| A + B | 0.06/0.12 | 97 |
|  | 0.06/0.25 | 100 |
|  | 0.06/0.50 | 99 |
|  | 0.12/0.12 | 97 |
|  | 0.12/0.25 | 99 |
|  | 0.12/0.50 | 100 |
|  | 0.19/0.12 | 99 |
|  | 0.19/0.25 | 100 |
|  | 0.19/0.50 | 97 |
|  | 0.25/0.12 | 100 |
|  | 0.25/0.25 | 100 |
|  | 0.25/0.50 | 100 |
| Untreated | 0 | 0 |

A = N-[2,4-dichloro-5-[4-(difluoromethyl)-4,5-dihydro-3-methyl-5-oxo-1H-1,2,4-triazol-1-yl]phenyl]methanesulfonamide
B = 2,4-dinitro-$N^3$,$N^3$-dipropyl-6-(trifluoromethyl)-1,3-benzenediamine Example 3

Pre-emergent herbicidal evaluation of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide on Johnson Grass The compositions of the present invention were tested for herbicidal efficacy in the following manner:

Test compositions were prepared by dilution of a 65% water-soluble granule (65 WG) formulation of 2,4-dinitro-$N^3$,$N^3$-dipropyl-6-(trifluoromethyl)-1,3-benzenediamine in a spray tank that provided the appropriate application rate of 2,4-dinitro-$N^3$,$N^3$-dipropyl-6-(trifluoromethyl)-1,3-benzenediamine. Test compositions were also prepared by dilution of a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide in a spray tank that provided the appropriate application rate of N-[2,4-dichloro-5-[4-(difluoromethyl)-4,5-dihydro-3-methyl-5-oxo-1H-1,2,4-triazol-1-yl]phenyl]methanesulfonamide. In addition, test compositions were prepared containing mixtures of a 65% water-soluble granule (65 WG) formulation of 2,4-dinitro-$N^3,N^3$-dipropyl-6-(trifluoromethyl)-1,3-benzenediamine and a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide with water that provided the specified rates of the two herbicides.

The application of each test composition was performed with pressurized back-pack sprayers, calibrated to spray between 10 and 15 gallons per acre.

The experimental design used randomized plots with one pre-emergent treatment either the day of planting or the day after planting and four to eight replications per test trial. The size of each experimental plot was 6 feet by 30 feet.

Percent control of the weed (Johnson Grass) was evaluated and averaged in each experimental plot at 14 days after treatment (DAT) of each test rate.

The results, shown as an average of the replications, were compared with results observed in untreated control plots in the same trials. The results are in Table 3 below.

TABLE 3

Control of Johnson Grass by Compositions of the Present Invention

| Treatment | Rate of Appln. (lb AI/Acre) | Control @ 14 DAT (%) |
|---|---|---|
| A | 0.06 | 42 |
|   | 0.12 | 67 |
|   | 0.19 | 65 |
|   | 0.25 | 70 |
| B | 0.12 | 42 |
|   | 0.25 | 48 |
|   | 0.50 | 77 |
| A + B | 0.06/0.12 | 49 |
|   | 0.06/0.25 | 73 |
|   | 0.06/0.50 | 80 |
|   | 0.12/0.12 | 64 |
|   | 0.12/0.25 | 81 |
|   | 0.12/0.50 | 86 |
|   | 0.19/0.12 | 67 |
|   | 0.19/0.25 | 82 |
|   | 0.19/0.50 | 86 |
|   | 0.25/0.12 | 72 |
|   | 0.25/0.25 | 83 |
|   | 0.25/0.50 | 86 |
| Untreated | 0 | 0 |

A = N-[2,4-dichloro-5-[4-(difluoromethyl)-4,5-dihydro-3-methyl-5-oxo-1H-1,2,4-triazol-1-yl]phenyl]methanesulfonamide
B = 2,4-dinitro-$N^3,N^3$-dipropyl-6-(trifluoromethyl)-1,3-benzenediamine Example 4

Pre-emergent herbicidal evaluation of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide on Barnyard Grass The compositions of the present invention were tested for herbicidal efficacy in the following manner:

Test compositions were prepared by dilution of a 65% water-soluble granule (65 WG) formulation of 2,4-dinitro-$N^3,N^3$-dipropyl-6-(trifluoromethyl)-1,3-benzenediamine in a spray tank that provided the appropriate application rate of 2,4-dinitro-$N^3,N^3$-dipropyl-6-(trifluoromethyl)-1,3-benzenediamine. Test compositions were also prepared by dilution of a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide in a spray tank that provided the appropriate application rate of N-[2,4-dichloro-5-[4-(difluoromethyl)-4,5-dihydro-3-methyl-5-oxo-1H-1,2,4-triazol-1-yl]phenyl]methanesulfonamide. In addition, test compositions were prepared containing mixtures of a 65% water-soluble granule (65 WG) formulation of 2,4-dinitro-$N^3,N^3$-dipropyl-6-(trifluoromethyl)-1,3-benzenediamine and a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide with water that provided the specified rates of the two herbicides.

The application of each test composition was performed with pressurized back-pack sprayers, calibrated to spray between 10 and 15 gallons per acre.

The experimental design used randomized plots with one pre-emergent treatment either the day of planting or the day after planting and four to eight replications per test trial. The size of each experimental plot was 6 feet by 30 feet.

Percent control of the weed (Barnyard Grass) was evaluated and averaged in each experimental plot at 14 days after treatment (DAT) of each test rate.

The results, shown as an average of the replications, were compared with results observed in untreated control plots in the same trials. The results are in Table 4 below.

TABLE 4

Control of Barnyard Grass by Compositions of the Present Invention

| Treatment | Rate of Appln. (lb AI/Acre) | Control @ 14 DAT (%) |
|---|---|---|
| A | 0.06 | 55 |
|   | 0.12 | 80 |
|   | 0.19 | 88 |
|   | 0.25 | 93 |
| B | 0.12 | 63 |
|   | 0.25 | 69 |
|   | 0.50 | 86 |
| A + B | 0.06/0.12 | 90 |
|   | 0.06/0.25 | 99 |
|   | 0.06/0.50 | 100 |
|   | 0.12/0.12 | 96 |
|   | 0.12/0.25 | 100 |
|   | 0.12/0.50 | 100 |
|   | 0.19/0.12 | 100 |
|   | 0.19/0.25 | 100 |
|   | 0.19/0.50 | 100 |
|   | 0.25/0.12 | 100 |
|   | 0.25/0.25 | 100 |
|   | 0.25/0.50 | 100 |
| Untreated | 0 | 0 |

A = N-[2,4-dichloro-5-[4-(difluoromethyl)-4,5-dihydro-3-methyl-5-oxo-1H-1,2,4-triazol-1-yl]phenyl]methanesulfonamide
B = 2,4-dinitro-$N^3,N^3$-dipropyl-6-(trifluoromethyl)-1,3-benzenediamine Example 5

Pre-emergent herbicidal evaluation of 2,4-dinitro-$N^3$,$N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide on Green Foxtail The compositions of the present invention were tested for herbicidal efficacy in the following manner:

Test compositions were prepared by dilution of a 65% water-soluble granule (65 WG) formulation of 2,4-dinitro- $N^3,N^3$-dipropyl-6-(trifluoromethyl)-1,3-benzenediamine in a spray tank that provided the appropriate application rate of 2,4-dinitro-$N^3,N^3$-dipropyl-6-(trifluoromethyl)-1,3-benzenediamine. Test compositions were also prepared by dilution of a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide in a spray tank that provided the appropriate application rate of N-[2,4-dichloro-5-[4-(difluoromethyl)-4,5-dihydro-3-methyl-5-oxo-1H-1,2,4-triazol-1-yl]phenyl]methanesulfonamide. In addition, test compositions were prepared containing mixtures of a 65% water-soluble granule (65 WG) formulation of 2,4-dinitro-$N^3,N^3$-dipropyl-6-(trifluoromethyl)-1,3-benzenediamine and a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide with water that provided the specified rates of the two herbicides.

The application of each test composition was performed with pressurized back-pack sprayers, calibrated to spray between 10 and 15 gallons per acre.

The experimental design used randomized plots with one pre-emergent treatment either the day of planting or the day after planting and four to eight replications per test trial. The size of each experimental plot was 6 feet by 30 feet.

Percent control of the weed (Green Foxtail) was evaluated and averaged in each experimental plot at 14 days after treatment (DAT) of each test rate.

The results, shown as an average of the replications, were compared with results observed in untreated control plots in the same trials. The results are in Table 5 below.

TABLE 5

Control of Green Foxtail by Compositions of the Present Invention

| Treatment | Rate of Appln. (lb AI/Acre) | Control @ 14 DAT (%) |
|---|---|---|
| A | 0.06 | 62 |
|   | 0.12 | 76 |
|   | 0.19 | 93 |
|   | 0.25 | 97 |
| B | 0.12 | 87 |
|   | 0.25 | 91 |
|   | 0.50 | 95 |
| A + B | 0.06/0.12 | 98 |
|   | 0.06/0.25 | 100 |
|   | 0.06/0.50 | 99 |
|   | 0.12/0.12 | 99 |
|   | 0.12/0.25 | 99 |
|   | 0.12/0.50 | 100 |
|   | 0.19/0.12 | 99 |
|   | 0.19/0.25 | 99 |
|   | 0.19/0.50 | 100 |
|   | 0.25/0.12 | 100 |
|   | 0.25/0.25 | 100 |
|   | 0.25/0.50 | 100 |
| Untreated | 0 | 0 |

A = N-[2,4-dichloro-5-[4-(difluoromethyl)-4,5-dihydro-3-methyl-5-oxo-1H-1,2,4-triazol-1-yl]phenyl]methanesulfonamide
B = 2,4-dinitro-$N^3,N^3$-dipropyl-6-(trifluoromethyl)-1,3-benzenediamine Example 6

Pre-emergent herbicidal evaluation of 2,4-dinitro-$N^3,N^3$-dipropyl-6-(trifluoromethyl)-1,3-benzenediamine and N-[2,4-dichloro-5-[4-(difluoromethyl)-4,5-dihydro-3-methyl-5-oxo-1H-1,2,4-triazol-1-yl]phenyl]methanesulfonamide on Annual Blue Grass The compositions of the present invention were tested for herbicidal efficacy in the following manner:

Test compositions were prepared by dilution of a 65% water-soluble granule (65 WG) formulation of 2,4-dinitro-$N^3,N^3$-dipropyl-6-(trifluoromethyl)-1,3-benzenediamine in a spray tank that provided the appropriate application rate of 2,4-dinitro-$N^3,N^3$-dipropyl-6-(trifluoromethyl)-1,3-benzenediamine. Test compositions were also prepared by dilution of a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide in a spray tank that provided the appropriate application rate of N-[2,4-dichloro-5-[4-(difluoromethyl)-4,5-dihydro-3-methyl-5-oxo-1H-1,2,4-triazol-1-yl]phenyl]methanesulfonamide. In addition, test compositions were prepared containing mixtures of a 65% water-soluble granule (65 WG) formulation of 2,4-dinitro-$N^3,N^3$-dipropyl-6-(trifluoromethyl)-1,3-benzenediamine and a 80% wettable powder (80 WP) formulation of N-[2,4-dichloro-5-[4-(difluoromethyl)-4,5-dihydro-3-methyl-5-oxo-1H-1,2,4-triazol-1-yl]phenyl]methanesulfonamide with water that provided the specified rates of the two herbicides.

The application of each test composition was performed with pressurized back-pack sprayers, calibrated to spray between 10 and 15 gallons per acre.

The experimental design used randomized plots with one pre-emergent treatment either the day of planting or the day after planting and four to eight replications per test trial. The size of each experimental plot was 6 feet by 30 feet.

Percent control of the weed (Annual Blue Grass) was evaluated and averaged in each experimental plot at 14 days after treatment (DAT) of each test rate.

The results, shown as an average of the replications, were compared with results observed in untreated control plots in the same trials. The results are in Table 6 below.

TABLE 6

Control of Annual Blue Grass by Compositions of the Present Invention

| Treatment | Rate of Appln. (lb AI/Acre) | Control @ 14 DAT (%) |
|---|---|---|
| A | 0.06 | 37 |
|   | 0.12 | 47 |
|   | 0.19 | 62 |
|   | 0.25 | 60 |
| B | 0.12 | 45 |
|   | 0.25 | 38 |
|   | 0.50 | 58 |
| A + B | 0.06/0.12 | 53 |
|   | 0.06/0.25 | 58 |
|   | 0.06/0.50 | 74 |
|   | 0.12/0.12 | 66 |
|   | 0.12/0.25 | 68 |
|   | 0.12/0.50 | 76 |
|   | 0.19/0.12 | 74 |
|   | 0.19/0.25 | 72 |
|   | 0.19/0.50 | 84 |
|   | 0.25/0.12 | 80 |
|   | 0.25/0.25 | 76 |
|   | 0.25/0.50 | 78 |
| Untreated | 0 | 0 |

A = N-[2,4-dichloro-5-[4-(difluoromethyl)-4,5-dihydro-3-methyl-5-oxo-1H-1,2,4-triazol-1-yl]phenyl]methanesulfonamide
B = 2,4-dinitro-$N^3,N^3$-dipropyl-6-(trifluoromethyl)-1,3-benzenediamine The terms "weed" and "weeds" refer to any unwanted vegetation in agricultural crops, turf and orchards, as well as, but not limited to, around buildings, along fences, roadways and rail lines.

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. An herbicidal composition comprising a first herbicide and a second herbicide in which the first herbicide is 2,4-dinitro-$N^3$,$N^3$-dipropyl-6-(trifluoromethyl)-1,3-benzenediamine and the second herbicide is N-[2,4-dichloro-5-[4-(difluoromethyl)-4,5-dihydro-3-methyl-5-oxo-1H-1,2,4-triazol-1-yl]phenyl]methanesulfonamide.

2. The composition according to claim 1 wherein the ratio of 2,4-dinitro-$N^3$,$N^3$-dipropyl-6-(trifluoromethyl)-1,3-benzenediamine to N-[2,4-dichloro-5-[4-(difluoromethyl)-4,5-dihydro-3-methyl-5-oxo-1H-1,2,4-triazol-1-yl]phenyl]methanesulfonamide is in the range of from 10:1 to 1:1.

3. The composition according to claim 2 wherein the ratio of 2,4-dinitro-$N^3$,$N^3$-dipropyl-6-(trifluoromethyl)-1,3-benzenediamine to N-[2,4-dichloro-5-[4-(difluoromethyl)-4,5-dihydro-3-methyl-5-oxo-1H-1,2,4-triazol-1-yl]phenyl]methanesulfonamide is in the range of from 7:1 to 2:1.

4. A method for controlling weeds comprising applying a composition of claim 1 to a locus where weeds are present or are expected to be present.

5. A method according to claim 4 wherein the ratio of 2,4-dinitro-$N^3$,$N^3$-dipropyl-6-(trifluoromethyl)-1,3-benzenediamine to N-[2,4-dichloro-5-[4-(difluoromethyl)-4,5-dihydro-3-methyl-5-oxo-1H-1,2,4-triazol-1-yl]phenyl]methanesulfonamide in the composition is in the range of from 10:1 to 1:1.

6. A method according to claim 5 wherein the ratio of 2,4-dinitro-$N^3$,$N^3$-dipropyl-6-(trifluoromethyl)-1,3-benzenediamine to N-[2,4-dichloro-5-[4-(difluoromethyl)-4,5-dihydro-3-methyl-5-oxo-1H-1,2,4-triazol-1-yl]phenyl]methanesulfonamide is in the range of from 7:1 to 2:1.

* * * * *